United States Patent
Hirano et al.

(10) Patent No.: US 7,428,971 B2
(45) Date of Patent: Sep. 30, 2008

(54) METHOD FOR SORTING AND RECOVERING FINE PARTICLE AND APPARATUS FOR RECOVERY

(75) Inventors: Ken Hirano, Tokushima (JP);
Yoshinobu Baba, Tokushima (JP)

(73) Assignee: Techno Network Shikoku Co., Ltd., Kagawa (JP)

( * ) Notice: Subject to any disclaimer, the term of this patent is extended or adjusted under 35 U.S.C. 154(b) by 0 days.

(21) Appl. No.: 10/533,109

(22) PCT Filed: Oct. 31, 2003

(86) PCT No.: PCT/JP03/14037
§ 371 (c)(1),
(2), (4) Date: Apr. 28, 2005

(87) PCT Pub. No.: WO2004/039501
PCT Pub. Date: May 13, 2004

(65) Prior Publication Data
US 2006/0163119 A1     Jul. 27, 2006

(51) Int. Cl.
*B03B 5/62* (2006.01)
(52) U.S. Cl. .................... 209/210; 209/142; 209/143; 209/208
(58) Field of Classification Search ............. 209/127.1, 209/129, 210, 143, 137, 135, 208, 638, 552, 209/139.1, 142; 210/748
See application file for complete search history.

(56) References Cited

U.S. PATENT DOCUMENTS

| | | | | |
|---|---|---|---|---|
| 3,808,550 A | * | 4/1974 | Ashkin | 372/97 |
| 4,887,721 A | * | 12/1989 | Martin et al. | 209/579 |
| 5,170,890 A | * | 12/1992 | Wilson et al. | 209/3.1 |
| 5,495,105 A | * | 2/1996 | Nishimura et al. | 250/251 |
| 6,573,491 B1 | * | 6/2003 | Marchitto et al. | 250/251 |
| 7,068,874 B2 | * | 6/2006 | Wang et al. | 385/16 |
| 2002/0160470 A1 | * | 10/2002 | Zhang | 435/173.1 |

(Continued)

FOREIGN PATENT DOCUMENTS

DE     101 57 032 A1     11/2001

(Continued)

OTHER PUBLICATIONS

Search Report dated Jul. 23, 2007, issued in corresponding European Application No. 03770113.3-2307 PCT/JP0314037.

*Primary Examiner*—Patrick Mackey
*Assistant Examiner*—Terrell H Matthews
(74) *Attorney, Agent, or Firm*—Westerman, Hattori, Daniels & Adrian, LLP.

(57) ABSTRACT

The present invention provides a fine-particle sorting technique that uses optical pressure (optical force) and that can be applied in place of heretofore known cell sorting techniques; and a fine-particle recovering technique therefor. The fine-particle recovering method of the present invention comprises directing a laser beam toward a flow path of fine particles in such a manner that the laser beam crosses the flow direction of the fine particles to thereby deflect the direction of movement of the fine particles to be recovered, in the direction of convergence of the laser beam. The sorting method of the present invention comprises performing flow cytometric sorting of fine particles according to the above recovering method of the present invention.

14 Claims, 6 Drawing Sheets
(2 of 6 Drawing Sheet(s) Filed in Color)

U.S. PATENT DOCUMENTS

2002/0181837 A1 * 12/2002 Wang et al. .................. 385/16

FOREIGN PATENT DOCUMENTS

| | | |
|---|---|---|
| JP | 04-370089 | 12/1992 |
| JP | 08-038882 | 2/1996 |
| JP | 2000-206011 | 7/2000 |
| WO | WO 02/087792 A1 | 11/2002 |

* cited by examiner (a) t = 0    (b) t = 0.13 [seconds after]    (c) t = 0.17 [seconds after]    (d) t = 0.21 [seconds after]

METHOD FOR SORTING AND RECOVERING FINE PARTICLE AND APPARATUS FOR RECOVERY

TECHNICAL FIELD

The present invention relates to a method for sorting and recovering-fine particles, such as cells, an apparatus for recovery, and a flow cytometry process and cell sorter using the method or apparatus.

BACKGROUND ART

A cell sorting technique based on flow cytometry has been known as a method for selecting specific individual cells or other fine particles from a group of cells or the like [e.g., Nakauchi, Hiromitsu (University of Tsukuba, medical immunology), supervision, "Flow Cytometry Jiyu Jizai (flexible flow cytometry)", a separate volume of "Cell Technology", Shujun-Sha, Jul. 1, 1999, pp. 3-23].

In this technique, a suspension of target cells combined with an antibody that has been previously labeled with a fluorescent dye or like substance is made to flow, and first, the target cells in the flow path are irradiated with an excitation light selected in accordance with the fluorescent dye used for labeling, and the wavelength and intensity of the fluorescence or scattered light emitted from each cell are analyzed to distinguish the target cells. Subsequently, a voltage is applied to the distinguished cells with specific properties to electrically charge the cells, which are then subjected to discrimination, quantification, static analysis, etc., by using deflecting electrodes.

Since the technique is capable of processing a large amount of cells at a high speed in the living state, it is widely applied in the fields of immunology, hematology, genetic engineering, etc., for harvesting and isolating various cultured cells, cloning and proliferating specific cells, fractioning cells that express a specific antigen on their surface, conducting a kinetic analysis of cell membrane molecules, analyzing chromosomes, and other purposes. In particular, the technique is becoming indispensable for analyzing cell kinetics. Besides, this technique is beginning to be used in the clinical field, for example, to analyze solid components of urine.

The cell analysis and separation device used in the flow cytometry cell sorting technique is called a cell sorter (fluorescence-activated cell sorter, FACS). This device has an analysis portion that performs the analysis of fluorescence or other light mentioned above, and a sorting portion provided downstream of the analysis portion. Typically, a droplet charging system is employed as the sorting portion.

The cell (particle) sorting by the droplet charging system is based on, for example, the following principle. Cells in droplets in which scattered light and fluorescence are detected upon irradiation with a laser beam are positively or negatively charged, immediately before the liquid flow containing the cells is divided into droplets. When the charged droplets containing cells are allowed to fall so as to pass between two polarizing electrode plates that are different in potential, the droplets are drawn to the polarizing plates and deflected. Since the droplets containing uncharged cells and drops containing cells other than the desired cells fall perpendicularly, droplets containing only the desired cells can be separated and recovered.

However, the technique using such a cell sorter requires an ultrasonic generator to produce droplets each containing one cell (particle), and thus has disadvantages in that the cell sorter is not only expensive but also requires complicated operation and maintenance procedures and is incapable of sorting various kinds of fine particles at a time. Specifically, when using electrode plates, the cells can be electrically distinguished only by charging either positively or negatively, and therefore only two types of cells can be distinguished. Further, since the flow cell and nozzle are used repeatedly, impurities may be mixed in. Furthermore, problems such as atmospheric contamination by hazardous substances may occur when ultrasonically atomizing the cell suspension during the cell sorting.

In order to solve the problems of cell sorters, such as the extremely high price, overly complicated operation and maintenance procedures, and admixture of impurities, a method has been proposed which can be performed at low cost without the admixture of impurities. In this method, a microfabridated channel is formed on a substrate made of glass or a polymeric material, and cells or like fine particles are placed in a liquid flow and subjected to flow cytometry in the channel, thereby sorting the desired fine particles (a technique using a microchip) (e.g., Anne. Y. Fu et al., "A microfabricated fluorescence-activated cell sorter", Nature Biotechnology, Vol. 17, November 1999, pp. 1109-1111; and Anne Y. Fu et al., "An Integrated Microfablicated Cell Sorter", Analytical Chemistry, Vol. 74, No. 11, Jun. 1, 2002, pp. 2451-2457).

In this cell sorting operation using a microchip, a T-shaped channel is formed, and the desired cells are sorted from other cells by switching the flow of the solution that carries the cells (flow path selection control).

However, in the proposed method, the flow of the liquid can be switched only once, and thus only one kind of fine particles can be separated. One idea is that switching the flow direction two or more times can separate multiple kinds of fine particles, but since the response time of switching the liquid flow is too long, two or more flow switching steps require two or more liquid feed pumps. The connection of the pumps to the chip and the opening and closing of the valves are too complicated to put the idea into practice.

DISCLOSURE OF THE INVENTION

The object of the present invention is to provide an improved sorting technique that is free of the disadvantages of heretofore known cell sorting techniques, such as the necessity of a device for forming droplets, and the incapability of sorting and recovering multiple kinds of target fine particles at a time; and to provide a fine-particle sorting and recovering apparatus for use in the technique.

The present inventor succeeded for the first time in developing a fine-particle sorting technique using optical pressure (or optical force), the technique being applicable in place of known flow cytometry techniques, in particular sorting techniques using a droplet charging system or using flow direction switching (flow path selection control).

The present invention provides the following items 1 to 13.

1. A method for sorting and recovering fine particles that are responsive to optical pressure, the method comprising emitting a laser beam to a flow path of a gas or liquid containing fine particles that are responsive to optical pressure and a component or components that are irresponsive to optical pressure, in such a manner that the laser beam crosses the flow direction of the gas or liquid, to selectively deflect the direction of movement of only the fine particles that are responsive to optical pressure, in the direction of convergence of the laser beam, thereby sorting the fine particles from the component or components that are irresponsive to optical pressure, and recovering the fine particles.

2. The method according to item 1, wherein the fine particles are selected from the group consisting of organic or inorganic polymeric materials, metals, cells, microorganisms and biopolymers, all of which are responsive to optical pressure.

3. A method for sorting and recovering target fine particles, comprising irradiating with a laser beam the target fine particles, which are responsive to optical pressure, in a flow path of a gas or liquid containing fine particles that are responsive to optical pressure and a component or components that are irresponsive to optical pressure, in such a manner that the laser beam crosses the flow direction of the gas or liquid, to selectively deflect the direction of movement of only the target fine particles in the direction of convergence of the laser beam, thereby sorting the target fine particles from other fine particles and the component or components that are irresponsive to optical pressure, and recovering the target fine particles.

4. The method according to item 3, wherein the flow path is a flow path of a liquid.

5. The method according to item 3, wherein the target fine particles are selected from the group consisting of organic or inorganic polymeric materials, metals, cells, microorganisms and biopolymers, all of which are responsive to optical pressure.

6. The method according to item 3, wherein the target fine particles are cells or microorganisms.

7. A flow cytometry process in which the method according to item 6 is used for sorting target cells.

8. An apparatus for recovering fine particles, comprising:
a collector for collecting fine particles that are responsive to optical pressure;
a laser beam emitter; and
a flow path for flowing a gas or liquid containing fine particles that are responsive to optical pressure and a component or components that are irresponsive to optical pressure, the flow path being disposed between the collector and laser beam emitter;
the collector having at least one chamber disposed so that the opening faces the flow path;
the laser beam emitter having at least one emitting aperture; and
the apparatus being configured so as to emit a laser beam from the emitting aperture toward the opening of the chamber of the collector in such a manner that the laser beam crosses the flow path and converges behind the opening.

9. The apparatus according to item 8, wherein the opening of the chamber of the collector and the emitting aperture of the laser beam emitter face each other, with the flow path interposing therebetween.

10. The apparatus according to item 8, wherein the laser beam emitter has at least two emitting apertures, and wherein the collector has chambers corresponding in number to the emitting apertures.

11. The apparatus according to item 8, further comprising detection and analysis portions for detecting and analyzing fine particles in the gas and liquid passing through the flow path.

12. The apparatus according to item 11, wherein the detection and analysis portions are linked to the laser beam emitter, so that the target fine particles are selected based on data obtained in the detection and analysis portions and that only the selected target fine particles are irradiated with the laser beam.

13. A cell sorter comprising the apparatus according to item 8 as a sorting portion.

The fine-particle sorting and recovering method as defined in items 1 and 2 and the fine-particle recovering apparatus as defined in item 8 use the optical pressure of a laser beam, and are capable of sorting fine particles that are responsive to optical pressure from a component or components that are irresponsive to optical pressure (including the gas or liquid used as a flow medium) and recovering the fine particles.

According to the target fine-particle sorting and recovering method as defined in items 3 to 6 and the cell sorter as defined in item 13, only target fine particles can be sorted from component or components (including fine particles that are responsive to optical pressure and component or components that are irresponsive to optical pressure) and recovered, by selecting only the target fine particles, which are responsive to optical pressure, by such a detection and analysis technique as employed in heretofore known flow cytometry processes and cell sorters, and irradiating the selected target fine particles with a laser beam in the same manner as in the method and apparatus according to items 1, 2 and 8.

The method and apparatus according to the present invention, and in particular those described in items 3 to 6 and 13, are capable of sorting and recovering multiple kinds of desired live cells (target cells) without causing destruction or other damage, from a population of cells with various properties and functions, based on the differences in size and structure (physical properties), differences in the substance used for labeling, etc. Therefore, the method and apparatus of the present invention are useful as assisting techniques for cloning specific cells, cloning growth/differentiation factor receptor genes and other purposes, and can be effectively used in the analysis of various cell functions and the cell kinetic analysis of cell membrane molecules, chromosome DNA molecules, etc. Further, the method and apparatus can be effectively applied not only in the field of cell technology but also in, for example, the clinical field, to analyze solid components of urine.

The apparatus of the present invention can be in the form of a microchip, and the method of the present invention can be carried out easily and simply using such a microchip. That is, the method and apparatus are more advantageous than the heretofore known FACS in that they do not require expensive and complicated procedures.

Moreover, when using the apparatus of the present invention, the discrimination of multiple kinds of fine particles, which has been difficult in heretofore proposed techniques involving fluid control with a microchip, can be performed very quickly (with a short response time), accurately and efficiently by one procedure. In particular, the use of the apparatus of the present invention is more advantageous than the heretofore proposed techniques involving microchip fluid control, in that the apparatus is capable of discriminating the target fine particles easily even when using a trace amount of a sample.

BRIEF EXPLANATION OF THE DRAWINGS

The patent or application file contains at least one drawing executed in color. Copies of this patent or patent application publication with color drawing(s) will be provided by the Office upon request and payment of the necessary fee.

In FIGS. 1(a) and (b), 2 indicates a flow path; 5, a flow path inlet; and 6, a flow path outlet. In FIG. 1(b), 1 indicates a collector; 1a and 1b, chambers provided in the collector; 3, a laser beam emitter; 3a, an emitting aperture; 3b, a laser beam; and 4, an outer wall.

In FIG. 2, 2 indicates the flow path; 5, the flow path inlet; 6, the flow path outlet; a, a sample (liquid or gas) feed port; b, a sample discharge port; and 3a, a laser beam emitting aperture. The number 7 indicates an Nd:VAN laser; 8, a beam expander; 9, a reflecting mirror 1; 10, a dichroic mirror 2; 11, a dichroic mirror 1; 12, an objective lens 1; 13, a mercury lamp; 14, an ND filter (neutral-density filter); 15, an excitation barrier filter; 16, a fluorescence barrier filter; 17, a reflecting mirror 2; 18, a laser beam cut-off filter; 19, a CCD camera 1; 20, an objective lens 2; and 21, a CCD camera 2.

FIG. 7 is a color photograph of part (the flow path and collector) of the fine-particle recovering apparatus, taken from the front and corresponding to FIG. 1(a). For clear understanding, red ink is passed through the flow path (2). The red spots on the right and left are the flow path inlet (5) and the flow path outlet (6), respectively, and the red line between the spots is the flow path (2). For producing the fine-particle recovering apparatus (chip), holes are made as the flow path inlet (5) and flow path outlet (6), in a 5-mm-thick PDMS substrate (60 mm×24 mm), as shown in FIG. 1(a), and a 50-μm-wide, 25-μm-deep channel linking the holes is formed as the flow path (2). Further, 35-μm-wide, 35-μm-deep, 25-μm-long cavities are formed perpendicular to the channel, as the chambers (1a, 1b). Subsequently, 100-μm-thick PDMS films (60 mm×24 mm) are applied to the substrate, so as to cover the channel. In this manner, the flow path (2) and collector with the chambers (1a, 1b) of the fine-particle recovering apparatus are formed.

Figure 1:
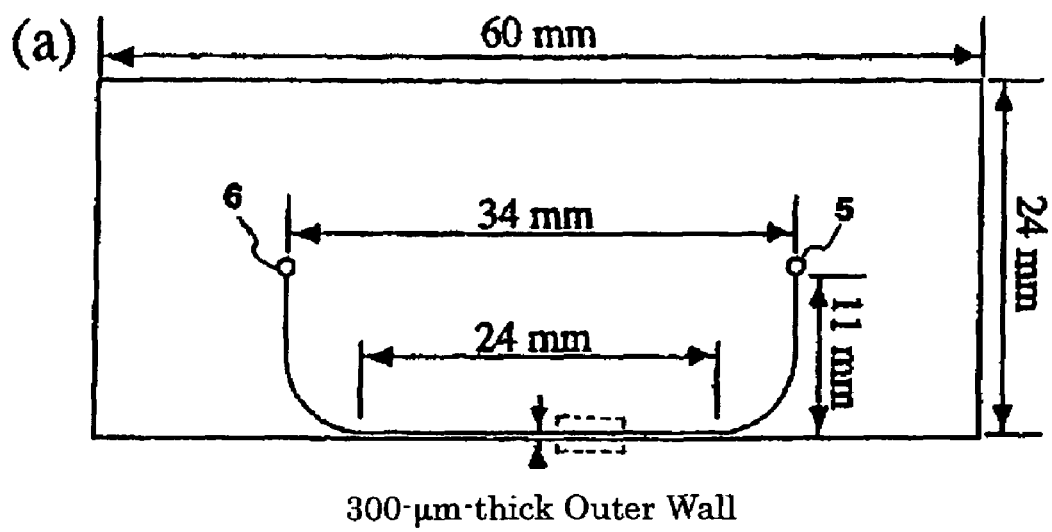
FIG. 1 is a set of schematic diagrams showing one embodiment of the fine-particle recovering apparatus according to the present invention (working example). (a) is a front elevation of part (the collector and flow path) of the apparatus; and (b) is an enlarged view of the portion enclosed in the dotted line in (a). (b) also shows the state of a laser beam (3b) emitted from a laser beam emitting aperture (3a).
Figure 1:
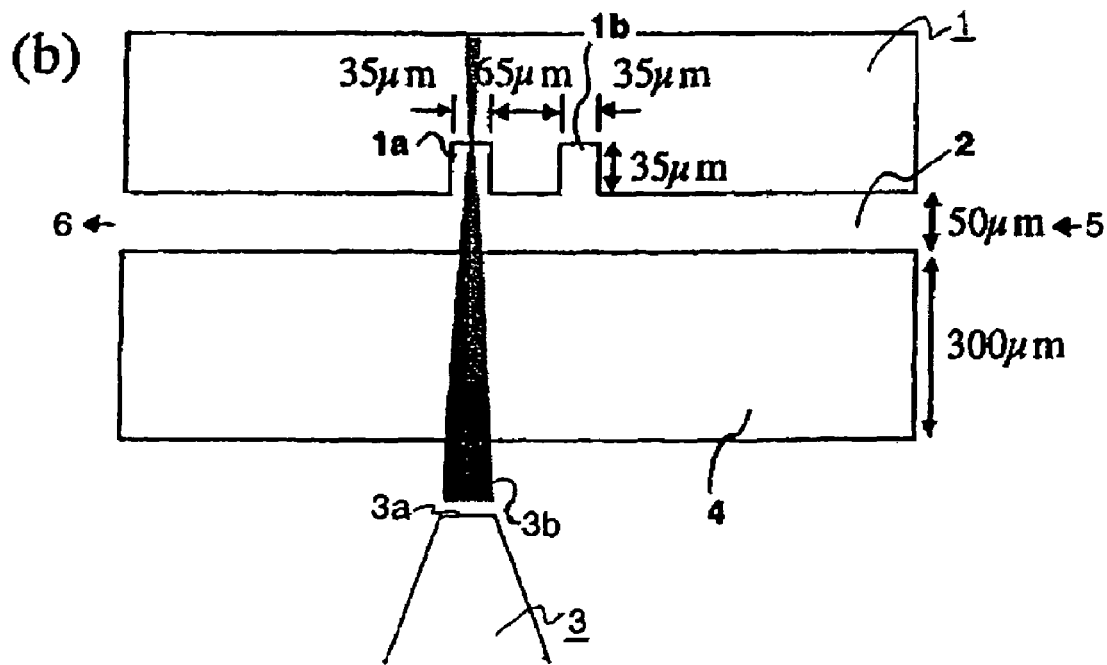

BEST MODE FOR CARRYING OUT THE INVENTION (1) Method for Sorting and Recovering Fine Particles The fine-particle sorting and recovering method of the present invention is described below in detail.

In the method of the present invention, a laser beam is first emitted to the flow path of a gas or liquid containing fine particles that are responsive to optical pressure, in such a manner that the laser beam crosses the flow direction of the gas or liquid, to thereby deflect the direction of movement of the fine particles to be recovered, which are passing through the flow path, in the direction of convergence of the laser beam.

The principle of this method is as follows. When the fine particles to be recovered flow into the irradiation area of the laser beam, in which the field of light is inhomogeneous, there arises a difference between the light force (light irradiation pressure, dielectrophoretic force and the like) acting on the fine particles and that acting on the substances surrounding them, due to the differences in the refractive index, dielectric constant and other factors between the fine particles and the substances surrounding them. Because of the difference in the light force, the fine particles move along the axial direction of the beam toward a position in which the field of light is dense, against the direction of hydrodynamic flow. This force is called optical pressure (optical force). Optical pressure becomes higher as the difference in the refractive index (or dielectric constant) between the fine particles and the media surrounding them becomes greater, and as the volume of the fine particles becomes greater. For example, a large optical pressure is generally produced on polystyrene particles (with a diameter of, for example, 1 μm), microorganisms, such as *Escherichia coli*, or cells of such microorganisms, suspended in water.

There have been examples of applying this principle to a laser trapping technique for capturing fine particles (e.g., Japanese Unexamined Patent Publications No. 1993-18887 and No. 1995-104191).

However, the known laser trapping technique is used merely for capturing fine particles at the focus of a laser beam converged with a lens, and no attempt is known to have been made to recover fine particles by deflecting the direction of movement (flow direction) of the fine particles using this technique, and more specifically, to recover fine particles by directing a laser beam toward the flow path of the fine particles so as to deflect the direction of movement of the fine particles in the direction of movement of the beam, against the flow direction.

Japanese Unexamined Patent Publication No. 1993-18887 discloses only the technique for capturing fine particles by holding a fine particle suspension in a chamber on, for example, a glass slide and irradiating with a laser beam the fine particles to be sampled, which are contained in the suspension. The captured fine particles are orientated in the direction of the electric field by electrostatic force, and then conveyed by moving the laser beam or the chamber. Japanese Unexamined Patent Publication No. 1995-104191 also teaches only an apparatus for trapping fine particles with a laser beam and controlling the position and direction (orientation) of the fine particles. Neither of the publications discloses a technique for deflecting the direction of movement of fine particles by the optical pressure of a laser beam and transferring the fine particles in the direction of convergence of the laser beam.

In the method of the present invention, any gas or liquid sample can be passed along the flow path as long as it contains fine particles on which optical pressure acts (which are responsive to optical pressure), as mentioned above. That is, any gas or liquid sample can be passed which comprises fine particles that are responsive to optical pressure and a component or components that are irresponsive to optical pressure as mentioned above. The gas or liquid used as a medium is included in the components that are irresponsive to optical pressure. The fine particles contained in the gas or liquid sample are different from the medium (gas or liquid) with regard to the refractive index, dielectric constant, etc., and thus receive a different amount of optical pressure. Typical examples of such fine particles include cells, microorganisms, biopolymer materials, etc. Examples of cells include animal cells (such as red blood cells) and plant cells. Examples of microorganisms include *Escherichia coli* and other bacteria; tobacco mosaic viruses and other viruses; yeast and other fungi; etc. Examples of biopolymer materials include chromosomes, ribosomes, mitochondria and other organelles forming various cells.

The fine particles that are responsive to optical pressure, which can be recovered by the method of the present invention, are not limited to the above and may be selected from various kinds of fine particles that are known to be trappable by a laser trapping technique, such as organic or inorganic polymeric materials and metals. Examples of organic polymeric materials include polystyrene, styrene-divinylbenzene, polymethyl methacrylate, etc. Examples of inorganic polymeric materials include glass, silica, magnetic materials, etc. Examples of metals include colloidal gold, aluminum, etc.

It is usually preferable that the fine particles have a particle diameter on the order of nanometers to micrometers, and more specifically a particle diameter of about 20 nm to about 50 μm. The fine particles are not limited in shape, size, mass, etc., and are generally spherical, but may be non-spherical, in shape.

Generally, the fine particles can be mixed with a gas or liquid that serves as a medium and made to pass along the flow path in the form of a liquid or gas flow. Usable media for forming the gas or liquid flow include various gases and liquids used in heretofore known laser trapping techniques. Examples of preferable media for forming the liquid flow (liquid media) include pure water, PBS (phosphate buffered saline), etc. Such media preferably have a refractive index smaller than that of the fine particles that are responsive to optical pressure (in this sense, the media are referred to as "components that are irresponsive to optical pressure" according to the present invention). A particularly preferable liquid sample to be passed along the flow path is, for example, a suspension obtained by mixing or suspending cells in the above-mentioned media. The number of cells in the liquid flow is not limited, and may usually be about $1 \times 10^5$/ml to $1 \times 10^7$/ml. The flow rate can be suitably selected according to the kind of fine particles, the type of laser beam to be emitted, etc., on the condition that the flow direction can be deflected by irradiation with the laser beam, in the direction of convergence of the laser beam.

The laser beam for use in the method of the present invention may be similar in type, irradiation conditions, etc., to laser beams used in heretofore known laser trapping techniques. Typical laser beams include Nd:YAG (neodymium-doped yttrium aluminum garnet) laser beams (wavelength: 1064 nm), Nd:VAN (neodymium-doped vanadate) laser beams (wavelength: 1064 nm), etc. Such laser beams are particularly preferable since they have little influence on organisms. A specific irradiation condition is 100 mW to 2 W in the case of a CW (continuous wave) beam. The laser beam can be emitted continuously or intermittently.

It is essential in the present invention to emit the laser beam so that it crosses the flow direction of the gas or liquid sample containing fine particles. The irradiation with the laser beam deflects the direction of movement of the fine particles in the gas or liquid flow, in the direction of movement (convergence) of the laser beam, against the flow direction of the gas or liquid. This makes it possible to sort the fine particles from a component or components that are irresponsive to optical pressure and recover the fine particles. For example, when a suitable chamber is disposed in the direction of convergence of the laser beam so that the opening of the chamber faces the flow path, only the desired fine particles are selectively collected and accumulated (concentrated) in the chamber.

It is generally preferable to emit the laser beam in a direction perpendicular to the direction of the gas or liquid flow. However, the angle of the laser beam is not limited as long as the laser beam crosses the direction of the gas or liquid flow, i.e., as long as it deflects the flow direction of the fine particles.

When multiple kinds of fine particles with different characteristics, which are responsive to optical pressure, are targeted, such fine particles (target fine particles) can be recovered in respective chambers, by, for example, disposing two or more of the chambers in parallel and emitting two or more laser beams toward the respective openings of the chambers.

(2) Method for Sorting and Recovering Target Fine Particles

The above-described fine-particle sorting and recovering method of the present invention can be applied to, for example, a sorting method employing flow cytometry. In other words, the method of the present invention can replace the conventional droplet charging system that serves as a sorting portion in flow cytometry. Flow cytometry employing the method of the present invention can selectively sort and recover predetermined fine particles (target fine particles).

Flow cytometry (cell sorting, FACS) employing the method of the present invention can be carried out by following a procedure such as that described below.

Scattered light (forward scattered light or side scattered light), fluorescence, etc., in a sample (gas or liquid) that contains the fine particles to be recovered (fine particles responsive to optical pressure), is detected and analyzed in advance by using the same kind of operation as that conducted with the detection portion and analysis portion of heretofore known flow cytometry. The sample (gas or liquid) containing the fine particles is then passed along a flow path by using the method of the present invention, and a laser beam is made to irradiate the selected fine particles to be recovered (target fine particles) flowing along the flow path in such a manner that the irradiation direction of the laser beam crosses the flow direction of the gas or liquid. When this is done, only the target fine particles are deflected from the moving direction toward the direction of convergence of the laser beam and sorted and recovered separately from other components or components that are irresponsive to optical pressure.

Preferable examples of the above-described target fine particles include cells bonded to (coated with) an antibody that is labeled with fluorochrome by means of the usual FACS, biopolymers labeled with fluorochrome, etc. The types of fine particles can be selected by using the same criteria as conventional FACS. For example, the intensity and wavelength of fluorescence, or the intensity of scattered light is detected by irradiation with an argon laser, and the fine particles that have the specific fluorescent intensity and wavelength, or the scattered light intensity that is desired for the target fine particles are selected by analyzing the detection results (data).

Moreover, if various target materials existing inside or on the surface of a cell, for example, proteins expressed in a cell, etc., are colored with two or more kinds of fluorochrome and, for example, GFP (green fluorescent protein) and like fluorescent proteins, it is possible to simultaneously select multiple kinds of fine particles having desired wavelengths as target fine particles. Such an operation may be the same as that conducted with the detection portion and analysis portion of heretofore known flow cytometry or cell sorters (for example, see "Flow Cytometry Jiyu Jizai," a separate volume of "Cell technology" edited by Hiromitsu Nakauchi (University of Tsukuba, medical immunology), Shujun-Sha, Jul. 1, 1999 (pp. 3-23).

The sorting method of the invention uses a small amount of solution as a sample to be passed along a flow path and can detect, sort, and recover fine particles contained in the sample, and therefore the sorting method of the invention can be suitably employed in an immunity detection system using antigen-antibody reaction. In this case, by using a fluorescent material to label the antibody to be used in advance, it is possible to selectively lead micrometer-order fine particles formed by immunoreactions such as an antigen-antibody reaction, etc., from the flow path to a chamber by irradiation with a laser beam. By measuring the fine particles that are sorted, recovered, and accumulated (concentrated) in the chamber, it is possible to detect immunoreacted material with high sensitivity. In particular, by using different types of fluorescent materials depending on the types of the antibody used in this method, it is possible to sort, recover and analyze multiple antigen antibody reactants (e.g., different cells, etc.) in a single step (multi-detection) based on differences in fluorescent intensity and wavelength.

If fluorescent labeling is not employed, it is possible to use different sizes of beads suitable for the types of antibody instead of the fluorescent material. In this case, after coating the beads with antibody, the antibody is subjected to immunoreaction by being mixed with a specimen, such as blood, and then a liquid containing the thus obtained reactants (fine particles) is used as a sample to be passed along a flow path. This makes it possible to sort, recover and analyze multiple types of antigen antibody reactants (e.g., different cells, etc.) in a single step depending on the size of the fine particles.

(3) Fine-particle Recovering Apparatus

The fine-particle recovering apparatus of the present invention comprises:

a collector for collecting fine particles that are responsive to optical pressure;

a laser beam emitter; and a flow path for passing a gas or liquid containing fine particles that are responsive to optical pressure and a component or components that are irresponsive to optical pressure, the flow path being disposed between the collector and laser beam emitter. The collector has at least one chamber that is disposed so that the opening faces the flow path, and the laser beam emitter has at least one emitting aperture. A laser beam is emitted from the emitting aperture toward the opening of the chamber of the collector, so as to cross the flow path and converge at a point farther than the opening of the chamber.

Figure 2:
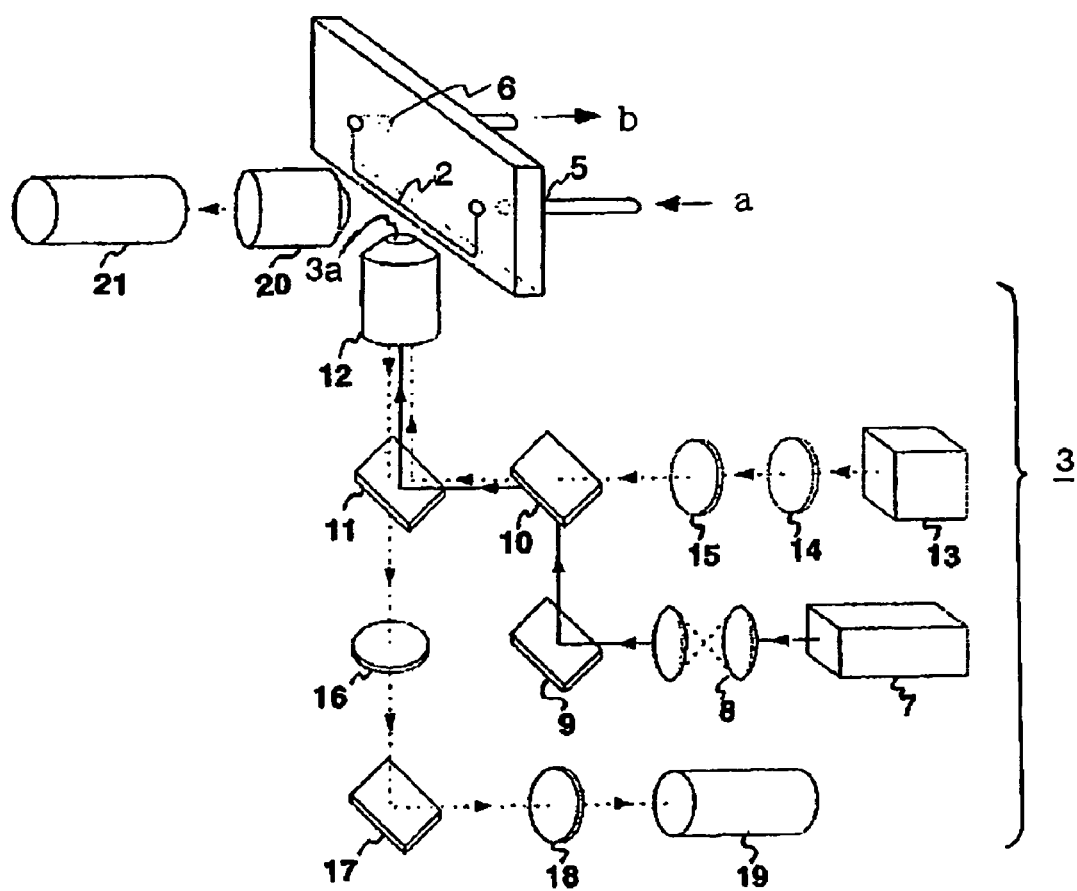
FIG. 2 is a schematic diagram of the fine-particle recovering apparatus shown in FIG. 1, in which the laser beam emitter (3) is illustrated in more detail.

FIGS. 1 and 2 are schematic diagrams of one embodiment of the fine-particle recovering apparatus of the present invention. The apparatus shown in these figures is in the form of a microchip for recovering fluorescent latex beads (with a diameter of about 2 μm), as described in detail in the Examples given hereinafter. FIG. 1(a) is a front elevation of the fine-particle recovering apparatus. FIG. 1(b) is an enlarged view of the portion enclosed in the dotted line in FIG. 1(a) and also shows the state of a laser beam (3b) being emitted from the emitting aperture (3a) of the laser beam emitter (3).

Figure 4:
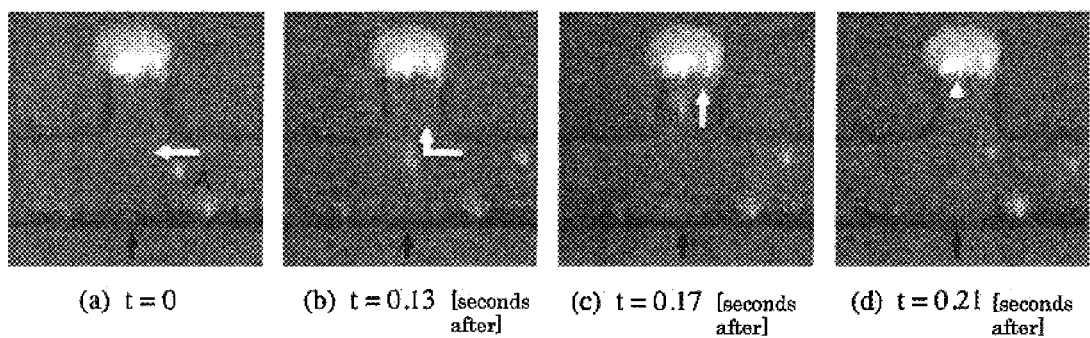
FIG. 4 is a set of color images showing the results of the test carried out in Example 1, and specifically, color photographs of the states of fluorescent latex beads A being collected in the chamber upon irradiation with a laser beam, the photographs being taken with the lapse of time.

The fine-particle recovering apparatus comprises a collector (1 in FIG. 1(b)) that has two chambers (1a and 1b in FIG. 1(b)); a laser beam emitter (3 in FIG. 1(b)) that has one emitting aperture (3a in FIG. 1(b)); and a flow path (2 in FIG. 1(b)) between the collector (1) and the laser beam emitter (3). The emitting aperture (3a) is disposed so as to face the opening of the chamber (1a) of the collector, with the flow path (2) interposing therebetween, so that the laser beam enters the chamber through the opening. The apparatus is configured so that the gas or liquid sample containing the fine particles to be recovered enters the flow path (2) from a in FIG. 2 through a flow path inlet (5), passes along the flow path (2) from the flow path inlet (5) to a flow path outlet (6), and is discharged from b through the flow path outlet (6). In FIG. 1(b), 4 is an outer wall that constitutes the bottom of the fine-particle recovering apparatus. The flow path (2) is formed between the outer wall and the collector (1).

The collector shown in FIG. 1 has chambers (1a, 1b) with a volume of 35 μm×25 μm (the area of the bottom or the opening)×35 μm (the distance from the opening to the bottom, i.e., depth). However, the volume of the chambers and the size of the openings of the chambers in the collector of the apparatus of the present invention are not limited to the above, and may be suitably selected according to the intended use of the apparatus, the size of the collector, the size and amount of the fine particles to be collected in each of the chambers, the diameter of the laser beam to be emitted, etc. The flow path (2) shown in FIG. 1 has a rectangular cross section of 50 μm×25 μm. However, the cross sectional shape and area (in other words, size) of the flow path (2) are not limited to the above, and can be suitably selected according to the form (gas or liquid) of the medium to be passed along the flow path, and according to the size of the fine particles and other factors.

The apparatus of the present invention recovers fine particles, for example, in the following manner. First, a gas or liquid sample (preferably a liquid sample) containing target fine particles is made to pass along the flow path from the flow path inlet (5) toward the flow path outlet (6). While the sample is passing along the flow path (2), the laser beam (3b) is emitted from the emitting aperture (3a) so as to condense in the chamber (1a). Thus, the laser beam emitted from the emitting aperture (3a) is directed toward the flow path (2) along which the gas or liquid sample containing the target fine particles is passing. When the target fine particles enter the laser beam irradiation area in the flow path (2), the direction of movement of the target fine particles is deflected in the direction toward the chamber (1a) by the action of the optical pressure of the laser beam. As a result, the target fine particles are collected in the chamber (1a).

FIG. 2 illustrates in further detail the laser beam emitter (3) of the fine-particle recovering apparatus of FIG. 1. However, the apparatus comprising the laser beam emitter (3) shown in FIG. 2 is one embodiment of the present invention, and the present invention is not limited thereto. In FIG. 2, 7 indicates an Nd:VAN laser; 8, a beam expander; 9, a reflecting mirror 1; 10, a dichroic mirror 2; 11, a dichroic mirror 1; 12, an objective lens 1; 13, a mercury lamp; 14, an ND filter (neutral-density filter); 15, an excitation barrier filter; 16, a fluorescence barrier filter; 17, a reflecting mirror 2; 18, a laser beam cut-off filter; and 19, a CCD camera 1.

In the embodiment shown in FIG. 2, the diameter of the laser beam emitted from the Nd:VAN laser (7) as a laser beam source is adjusted by the beam expander (8) located ahead of the laser (7) in the direction of movement of the laser beam. Subsequently, the laser beam is bent by the reflecting mirror 1 (9), dichroic mirror 2 (10) and dichroic mirror 1 (11), passed through the objective lens 1 (12), and radiated from the emitting aperture (3a) toward the opening of the chamber (1a) of the collector. This causes the laser beam (3b) from the Nd:VAN laser (7) to condense in the chamber (1a).

It is desirable that the laser beam be adjusted so as to converge at a point farther than the opening of the chamber, preferably in the vicinity of the bottom of the chamber. The laser beam can be converged using an objective lens, as mentioned above. The objective lens 1 (12) in FIG. 2 is vertically movable, and the convergence position of the laser beam can be vertically adjusted by the movement of the lens 1 (12). As described above, the convergence position of the laser beam is not limited as long as it is farther than the opening of the chamber of the collector (1), and may be inside or outside the chamber, and preferably in the vicinity of the bottom of the chamber, irrespective of whether it is inside or outside the chamber.

The laser beam to be used is usually circular, but is not limited thereto and may be elliptic.

In a preferable embodiment of the apparatus of the present invention, the opening of the chamber of the collector faces the emitting aperture of the laser beam emitter, with the flow path interposing therebetween, as shown in FIG. 1. According to this embodiment, the laser beam is radiated perpendicularly to the flow path, i.e., the flow of the gas or liquid containing target fine particles. However, the disposition of the chamber of the collector and the emitting aperture of the laser beam emitter can be determined as desired, as long as the laser beam crosses the flow path and enters the opening of the chamber of the collector.

Another preferable embodiment of the apparatus of the present invention comprises a laser beam emitter that has two or more emitting apertures, and a collector that has two or more chambers corresponding in number to the emitting apertures. With such an apparatus, multiple kinds of target fine particles, which are responsive to optical pressure, can be sorted and collected in respective chambers.

Figure 3:
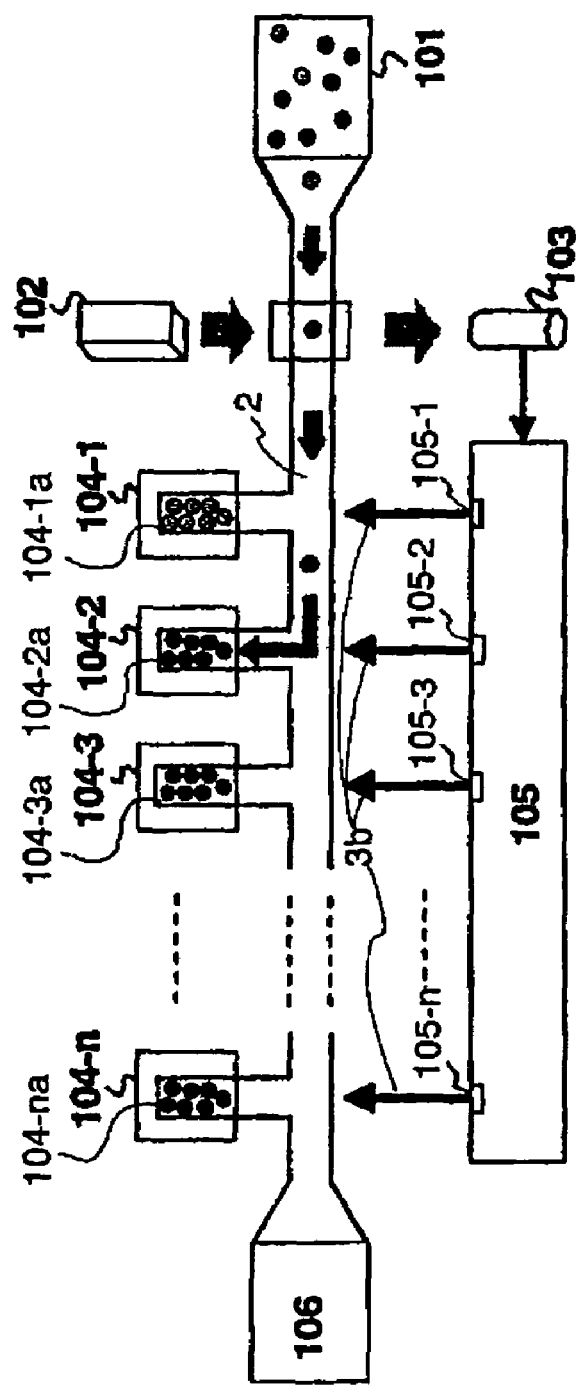
FIG. 3 is a schematic diagram showing one embodiment of the fine-particle recovering apparatus of the present invention suitable for multiple recovery and multiple detection (multiple sort apparatus). In the figure, 101 indicates a reservoir that holds a liquid or gas sample containing target fine particles; and 104-1,104-2,104-3 and 104-n, collector units provided with chambers 104-1a, 104-2a, 104-3a and 104-na, respectively. The number 105 indicates a laser beam controller including a laser beam emitter; and 105-1,105-2,105-3 and 105-n, emitting apertures provided in the laser beam emitter. The number 2 denotes a flow path; 106, a discharge reservoir for recovering the sample; 3b, a laser beam; 102, a detection laser; and 103, a detector.

FIG. 3 shows a schematic diagram of an example of such a multiple sorting apparatus. In this figure, 101 indicates a reservoir holding a liquid or gas sample containing target fine particles to be recovered; and 104-1, 104-2, 104-3 . . . 104-n indicate collector units that have chambers (104-1a, 104-2a, 104-3a . . . 104-na), respectively (which correspond to the collector (1) that has the chambers (1a, 1b) in FIG. 1). The number 105 denotes a laser beam controller including a laser beam emitter (which corresponds to the laser beam emitter (3) in FIG. 1). The collector has two or more chambers (104-1a, 104-2a, 104-3a . . . 104-na) corresponding in number to the two or more emitting apertures (105-1, 105-2, 105-3 . . . 105-n) provided in the laser beam emitter. The number 2 indicates a flow path along which the sample passes, and 106, a discharge reservoir for recovering the sample.

The fine-particle recovering apparatus of this embodiment preferably comprises detection and analysis portions for detecting and analyzing fine particles that are responsive to optical pressure, in the gas or liquid passing along the flow path, in addition to the laser beam emitter, collector and flow path. In this case, the portion comprising the laser beam emitter, collector and flow path can be called a sorting portion as distinguished from the detection and analysis portions. The device comprising the sorting portion and detection and analysis portions is a cell sorter. In FIG. 3, 102 and 103 correspond to the detection portion, and indicate a detection laser and detector, respectively; and the analysis portion is incorporated in the laser controller (105).

The detection and analysis portions of the apparatus of this embodiment may be similar to those used in heretofore known flow cytometry techniques and cell sorters. For example, the detection portion may have a detector for measuring the light of forward scatter (FSC) or side scatter (SSC) obtained from fine particles in a sample (a liquid or gas sample, and preferably a liquid sample) passing along a flow path (liquid flow or gas flow) by emitting a laser beam (e.g., argon, diode, dye, helium neon or like single or dual laser) to the sample; or may have a detector for measuring various types of fluorescence obtained from fluorescence-labeled fine particles when target fine particles have been previously labeled with a fluorescent material. The analysis portion may have an analysis display for displaying a cytogram or histogram obtained by digital conversion of the data detected by the detector. The light intensities of forward scatter (FSC) and side scatter (SSC) vary depending on, for example, the size of cells and the complexity of the internal structure of cells, respectively. Fluorescent materials for labeling target fine particles in flow cytometry or cell sorters are well known, and such fluorescent materials can be used in the present invention in a similar manner as in the heretofore known techniques [e.g., Nakauchi, Hiromitsu (University of Tsukuba, medical immunology), supervision, "Flow Cytometry Jiyu Jizai", a separate volume of "Cell Technology", Shujun-Sha, Jul. 1, 1999, pp. 3-23].

One preferable embodiment of the apparatus of the present invention is designed so that the detection and analysis portions are linked to the laser beam emitter in the sorting portion, and that only when selected target fine particles flow into an area to be irradiated in the flow path, the laser beam selectively irradiates the target fine particles, based on the data obtained in the detection portion and analyzed in the analysis portion.

Use of such a preferable apparatus according to the present invention makes it possible to distinguish, sort and recover one or more kinds of target fine particles from a sample (a gas or liquid sample) containing two or more kinds of fine particles that are responsive to optical pressure, based on the characteristics of each kind of fine particles.

Described below is an example of a method for sorting and recovering target fine particles using the apparatus of the present invention shown in FIG. 3.

A fluorescence-labeled antibody is bound to each of different kinds of target fine particles (e.g., cells, microorganisms, proteins, etc.) by an immunoreaction, such as an antigen-antibody reaction, and a sample liquid containing the target fine particles (e.g., a suspension of cells or the like) is made to flow linearly at a high flow rate using a nozzle or like means. When a laser beam is emitted to the flowing sample liquid, the target fine particles in the liquid flow generate scattered light and fluorescence. The detection portion measures the intensity of these lights, fluorescence wavelength, etc., and the analysis portion analyzes the measurement results. Subsequently, the laser controller (105) determines the position, timing and other conditions of laser beam irradiation, based on the obtained information (data), so that the target fine particles are selectively irradiated with the laser beam when they pass along the flow path (2). The flow direction of the target fine particles irradiated with the laser beam is deflected by optical pressure, and the target fine particles are collected in the chambers of the collector units. Thus, multiple kinds of target fine particles can be separately sorted based on the differences in the intensity and wavelength of the scattered light and fluorescence generated, and collected in respective chambers (104-1 . . . 104-n). The fine particles (e.g., cells, microorganisms, proteins or the like) collected in the chambers can be immunoassayed by detecting an immunoreaction in each chamber or by removing the fine particles from the chambers and subjecting them separately to a biochemical analysis using a standard process.

In the above method, laser beam emitting apertures may be provided in a number corresponding to that of the chambers, or alternatively, the direction of one laser may be varied by a known laser operation technique using a polygon mirror or like means, to operate and control the position and timing of laser irradiation.

Each kind of target fine particles is recovered as a result of the deflection of the flow direction of the target fine particles by the optical pressure of the laser beam emitted from each laser beam emitting aperture. The position of the flow direction deflection of the target fine particles can be determined by controlling the laser beam emitting aperture or by moving the position of the collector or chamber while fixing the position of the emitting aperture.

The apparatus shown in FIG. 3 can be applied to the recovery of cells with different types of fluorescence information in separate chambers according to the type of fluorescence information (multi-sorting). In this case, each kind of cells collected in each chamber can also be analyzed in the chamber or after being removed from the chamber. Such an apparatus of the present invention makes it possible to sort and recover different kinds of cells simultaneously using one apparatus (for example, using one chip when the apparatus is in the form of a chip).

Effects of the Invention

As described above, the recovering method and apparatus of the present invention make it possible to recover fine particles that are responsive to optical pressure in a predetermined chamber by using optical pressure to make the fine particles to deflect and shift toward the direction of convergence of a laser beam. The method and apparatus of the invention make it possible to sort target fine particles from multiple kinds of fine particles by using a detection and/or analysis technique employed in heretofore-used flow cytometry or cell sorters (multiple sort and recovering devices). The optical pressure used in the present invention can be easily controlled and is advantageous in that the use thereof can simplify the apparatus and its peripherals. In a heretofore-used droplet charging system, fluid must be in the form of droplets; however, there is no need for fluid control in the fine-particle sorting technique using the method and apparatus of the present invention, and therefore it is possible to sort the target fine particles by using a small amount of sample.

EXAMPLES

The following Example is intended to illustrate the present invention in further detail.

Example 1

(1) Experimental Method

In this experiment, a fine-particle recovering apparatus (in the form of a microchip) of the present invention as shown in FIGS. 1 and 2 was used.

A fine-particle collector (1) provided on a chip comprises two microgrooves (35 μm×35 μm×25 μm, chambers (1a) and (1b)) for recovering fine particles. A microchannel (50 μm in width×25 μm in depth, flow path (2)) for allowing a sample containing fine particles to pass along is separated from the outside by an outer wall (4) (prepared by PDMS). Considering the working distance of the objective lens 1 (12 in FIG. 2), the thickness of the outer wall (4) was set at 300 μm so that an Nd:VAN laser beam (wavelength: 1064 nm) would converge on the bottom of the chamber (1a)(microgroove).

In this experiment, an inverted fluorescence microscope (Axiovert 135TV, manufactured by Carl Zeiss) was used in combination with a laser operation system. A laser beam emitted from an Nd:VAN laser (7) was condensed using the microscope objective lens (12) that faces the outer wall (4), and was introduced in the chamber (1a). The beam diameter was adjusted by introducing a beam expander (8) into the laser beam path, and the focus point of the laser and the observed face were aligned in the same objective lens.

Moreover, in order to observe the behavior of the fine particles flowing along the flow path (2) and to photograph fluorescence images of these fine particles, another objective lens 2 (20) and a color CCD camera 2 (21) were installed horizontally. The CCD camera 2 (21) makes it possible to take images of fine particles, with the fine particles having changed their traveling direction in the flow path (2) and being introduced into the chamber (1a). Moreover, a CCD camera 1 (19) was positioned so as be able to photograph the recovered fine particles in the chamber from the bottom.

In this experiment, fluorescent latex beads (manufactured by Polysciences, Inc.) having a diameter of 2 μm were used as fine particles responsive to optical pressure. A liquid prepared by suspending the fine particles in ultrapure water so that the concentration thereof became $1 \times 10^5$/ml was used as a sample liquid. The sample liquid was introduced into the flow path (2) from a flow path inlet (5) through (a) using a syringe pump (syringe feeder). The velocity of the sample liquid passing along the flow path (2) was 192 μm/second. The sample liquid that passed along the flow path (2) was recovered in (b) through a flow path outlet (6).

The laser beam (3b) was condensed in a chamber (1a), which is one of the two chambers (1a, 1b). The chamber (1a) was used as a chamber for recovering fine particles and the other chamber (1b) was used as a negative control chamber.

(2) Results

A specific fluorescent latex bead A was focused upon and the motion of the fluorescent latex bead in the flow path was followed. FIG. 4 shows the results. In FIG. 4, the black arrow ↑ indicates the location and the direction of the laser beam irradiation light, and the white arrow indicates the location and the moving direction of bead A. As is clear from FIG. 4, when bead A (see FIG. 4(a), which is defined as the condition of t=0) passed along the liquid current through the flow path and reached a laser beam irradiation region (see FIG. 4(b), which is defined as t=0.13), the moving direction of bead A was deflected toward the traveling direction of the beam (see FIG. 4(c), t=0.17), and bead A entered a chamber in the collector (see FIG. 4(d), t=0.21). In other words, when the 2-μm fluorescent bead that was passing along the flow path reached the irradiation region of the Nd:VAN laser beam (1600 mW), against the flow caused by hydrodynamic force and gravity, the fluorescent bead was deflected along the optical axis of the beam by optical pressure, shifted in the direction in which the irradiated beam was focused, and recovered in a chamber.

With this method, it is possible to sort target fine particles and recover them in respective chambers by turning the laser beam irradiation on or off.

Figure 5:
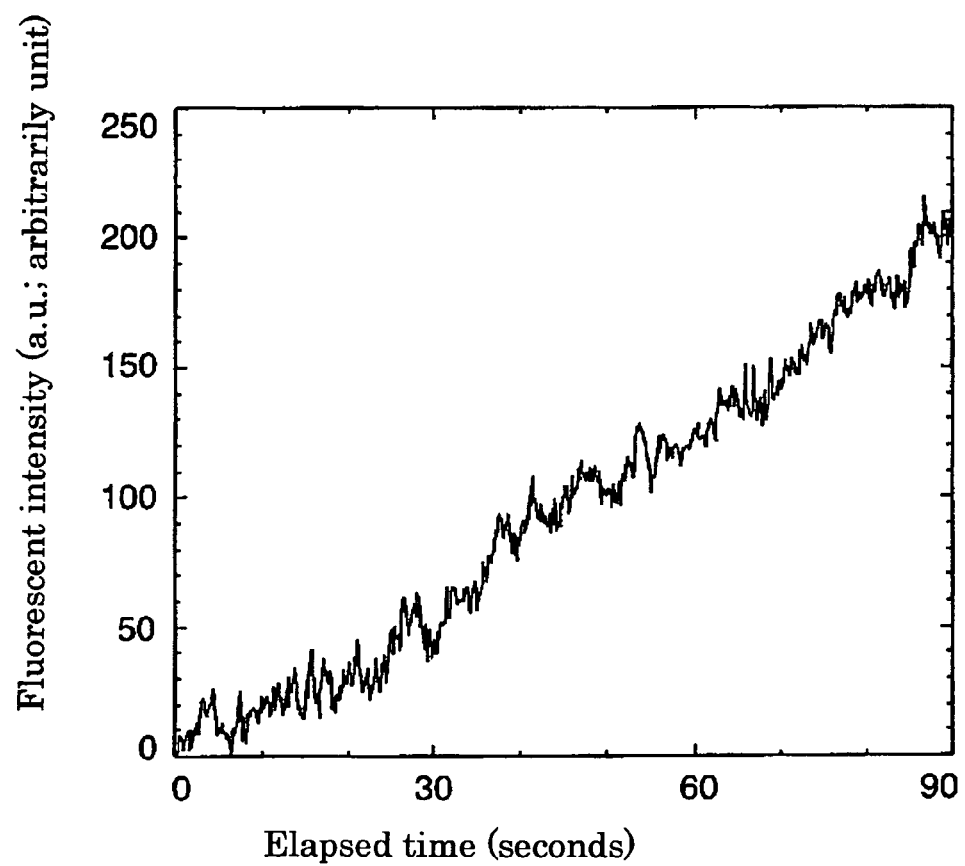
FIG. 5 is a graph showing the change in fluorescence intensity in a chamber in the test carried out in Example 1, the graph indicating that fine particles were collected and accumulated in the chamber with the lapse of time. The elapsed time (laser beam irradiation time; seconds) is plotted along the abscissa, and the relative value (a.u.: arbitrary unit) of the fluorescence intensity in the chamber is plotted along the ordinate.

In order to confirm the presence of the optical recovering ability of this method, a test was conducted to determine whether or not the fluorescent latex beads passing along the flow path could be recovered and accumulated (concentrated) in the chamber with the lapse of time. In other words, while keeping the laser beam continuously on, the fluorescence intensity in the chamber (1a)(35 μm×35 μm×25 μm) was measured over time. FIG. 5 shows the obtained results.

Note that the fluorescence intensity was obtained by downloading the images recorded on a videotape to a computer, and analyzing the fluorescence intensity of a certain region in the chamber for every video-frame (30 frames per second) using image-analysis software (NIH image: http://rsb.info.nih.gov/nih-image/). The obtained values are relative values (in FIG. 5, a.u. stands for arbitrary unit).

FIG. 5 is a graph showing the change in the above-mentioned fluorescence intensity in the chamber (1a) with elapsed time (in seconds), wherein the abscissa indicates elapsed time (duration of laser beam irradiation) and the ordinate indicates the fluorescence intensity (unit: a.u.).

As is clear from the results shown in FIG. 5, the fluorescence intensity in the chamber (1a) increased in proportion to the elapsed time for 90 seconds. This clearly shows that the target fine particles can be recovered and accumulated (concentrated) in a chamber by keeping the laser beam continuously on so as to deflect the flow of the fine particles passing along the flow path by the optical pressure toward the chamber.

Figure 6:
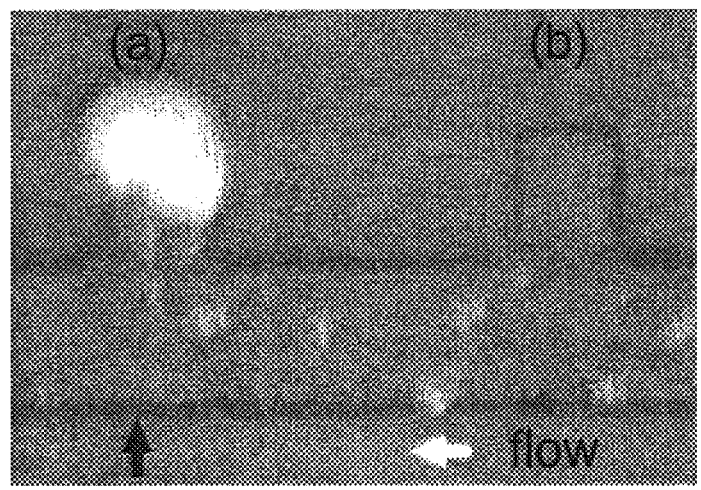
FIG. 6 is a photograph of the chamber (1a) and the negative control chamber (1b), taken 90 seconds after irradiation with a laser beam in the test carried out in Example 1.
Figure 7:
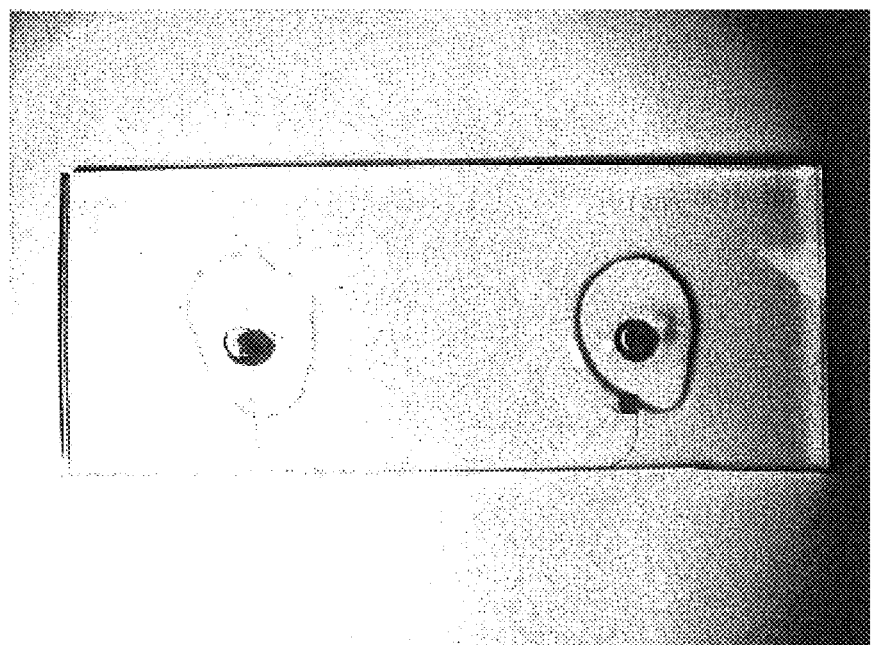
FIG. 7 is a set of color photographs corresponding to FIG. 1(a), which were taken from the front of the fine-particle recovering apparatus.

A photograph taken 90 seconds later by the CCD camera is shown in FIG. 6. In FIG. 6, (a) is the recovering chamber (1a) and (b) is the recovering chamber (1b). The white arrow, "flow", shows the direction of flow of the liquid (sample liquid) containing the fluorescent latex bead in the flow path, and the black arrow shows the radiation direction of the laser beam.

As shown in FIG. 6, the chamber (1a) was filled with fluorescent beads to about ⅓ of its capacity. In contrast, in the negative control chamber (chamber (1b)) toward which the optical pressure attributable to the laser beam had no effect, no fluorescence was observed and it was confirmed that no latex beads were recovered. This result proves that a series of recovery and concentration occurred based on the deflection and shift of fine particles caused by optical pressure (due to laser beam irradiation).

INDUSTRIAL APPLICABILITY

The present invention provides a method and apparatus for recovering fine particles such as cells, and flow cytometry and a cell sorter using the method and apparatus of the present invention.

The recovering method and apparatus of the present invention are useful as assisting techniques for cloning specific cells, cloning growth/differentiation factor receptor genes, etc., and can also be effectively used in the analysis of various cell functions and in the kinetic analysis of cell membrane molecules, chromosome DNA molecules, etc. Further, the method and apparatus can be effectively applied not only in the field of cell technology but also in, for example, the clinical field.

The invention claimed is:

1. A method for sorting and recovering fine particles that are responsive to optical pressure, the method comprising
    using an apparatus for recovering fine particles comprising
        a laser beam emitter that has two or more emitting apertures and a collector that has two or more chambers corresponding in number to the number of emitting apertures, emitting each laser beam from the laser beam emitter to a flow path of a gas or liquid containing
        fine particles that are responsive to optical pressure and
        a component or components that are irresponsive to optical pressure, in such a manner that the laser beam crosses the flow direction of the gas or liquid, to selectively deflect the direction of movement of only the fine particles that are responsive to optical pressure, in the direction of convergence of the laser beam, while adjusting the laser beam so as to converge inside each chamber of the collector facing each laser beam emitting aperture with the flow path interposing therebetween,
    thereby sorting the fine particles from the component or components that are irresponsive to optical pressure, and recovering the fine particles in the chambers of the collector.

2. The method according to claim 1, wherein the fine particles are selected from the group consisting of organic or inorganic polymeric materials, metals, cells, microorganisms and biopolymers, all of which are responsive to optical pressure.

3. A method for sorting and recovering target fine particles, comprising
    using an apparatus for recovering fine particles comprising
        a laser beam emitter that has two or more emitting apertures and a collector that has two or more chambers corresponding in number to the emitting apertures, irradiating with each laser beam from the laser beam emitter the target fine particles, which are responsive to optical pressure, in a flow path of a gas or liquid containing
        fine particles that are responsive to optical pressure and
        a component or components that are irresponsive to optical pressure, in such a manner that the laser beam crosses the flow direction of the gas or liquid, to selectively deflect the direction of movement of only the target fine particles in the direction of convergence of the laser beam, while adjusting the laser beam so as to converge inside each chamber of the collector facing each laser beam emitting aperture with the flow path interposing therebetween,
    thereby sorting the target fine particles from other fine particles and the component or components that are irresponsive to optical pressure, and recovering the target fine particles in the chambers of the collector.

4. The method according to claim 3, wherein the flow path is a flow path of a liquid.

5. The method according to claim 3, wherein the target fine particles are selected from the group consisting of organic or inorganic polymeric materials, metals, cells, microorganisms and biopolymers, all of which are responsive to optical pressure.

6. The method according to claim 3, wherein the target fine particles are cells or microorganisms.

7. A flow cytometry process in which the method according to claim 6 is used for sorting target cells.

8. An apparatus for recovering fine particles, comprising:
    a collector for collecting fine particles that are responsive to optical pressure;
    a laser beam emitter; and
    a flow path for flowing a gas or liquid containing
        fine particles that are responsive to optical pressure and
        a component or components that are irresponsive to optical pressure, the flow path being disposed between the collector and the laser beam emitter;

the collector having chambers corresponding in number to the emitting apertures, which are disposed so that the opening faces the flow path;

the laser beam emitter having at least two emitting apertures; and the apparatus being configured so as to emit a laser beam from each emitting aperture toward the opening of each chamber of the collector in such a manner that the laser beam crosses the flow path and converges inside the opening.

9. The apparatus according to claim 8, further comprising detection and analysis portions for detecting and analyzing fine particles in the gas and liquid passing through the flow path.

10. The apparatus according to claim 9, wherein the detection and analysis portions are linked to the laser beam emitter, so that the target fine particles are selected based on data obtained in the detection and analysis portions, and so that only the selected target fine particles are irradiated with the laser beam.

11. A cell sorter comprising the apparatus according to claim 8 as a sorting portion.

12. The method according to claim 1, wherein the fine particles responsive to optical pressure are recovered by changing the position of a collector or the chamber thereof, with the position of the laser beam emitting aperture being fixed.

13. The method according to claim 3, wherein the target particles are recovered by changing the position of a collector or the chamber thereof, with the position of the laser beam emitting aperture being fixed.

14. The apparatus according to claim 8, wherein the fine particles responsive to optical pressure are recovered by changing the position of a collector or the chamber thereof, with the position of the laser beam emitting aperture being fixed.

\* \* \* \* \*

UNITED STATES PATENT AND TRADEMARK OFFICE
CERTIFICATE OF CORRECTION

PATENT NO. : 7,428,971 B2  Page 1 of 1
APPLICATION NO. : 10/533109
DATED : September 30, 2008
INVENTOR(S) : Ken Hirano et al.

It is certified that error appears in the above-identified patent and that said Letters Patent is hereby corrected as shown below:

On the cover page:

Insert

Item --(30)   Foreign Application Priority Data

November 1, 2002   (JP) ................2002-320103--

Signed and Sealed this

Sixth Day of October, 2009

David J. Kappos
*Director of the United States Patent and Trademark Office*